United States Patent [19]
Lempriere

[11] Patent Number: 4,758,467
[45] Date of Patent: Jul. 19, 1988

[54] DISPOSABLE PERSONAL WASHING CLOTH

[76] Inventor: Noel D. Lempriere, 1144 Hilary Place, North Vancouver, Canada

[21] Appl. No.: 19,376

[22] Filed: Feb. 26, 1987

[51] Int. Cl.⁴ .............................................. A47L 1/15
[52] U.S. Cl. ................................... 428/290; 252/8.7; 252/91; 427/394; 427/430.1
[58] Field of Search ............ 428/290; 427/394, 430.1; 252/8.7, 91

[56] References Cited
U.S. PATENT DOCUMENTS
4,666,621  5/1987  Clark et al. ..................... 428/290

Primary Examiner—Marion C. McCamish
Attorney, Agent, or Firm—Scrivener and Clarke

[57] ABSTRACT

There is disclosed a single-use disposable impregnated dry cloth which can be presented dry to a user for use as a hair and body shampoo and wash cloth for use when showering. It comprises a high wet-strength nonwoven material impregnated with a surfactant composition. The preferred surfactant composition includes a fatty alcohol polyglycol ether sulphosuccinate, a foam booster, a super fatting agent and a fungicide.

10 Claims, No Drawings

DISPOSABLE PERSONAL WASHING CLOTH

This invention relates to a disposable personal washing cloth.

Bar soaps, shampoos and shower gels are well known articles for personal cleaning use in showers. These are generally used in conjunction with a sponge or cloth for ease of use. This method of cleaning in a shower however has disadvantages as messy bars of soap and bulky bottles need to be carried, which is generally inconvenient and cumbersome, especially when showering outside the home. One article which is currently known is the leaf, which overcomes these problems but is relatively costly and limited in its performance. We have now devised an improved personal washing article.

According to the present invention there is provided a single use disposable impregnated dry cloth comprising a high wet strength nonwoven substrate, impregnated with a mixture of surfactants and other agents and presented dry to the user for use as a hair and body shampoo and wash cloth for use when showering.

The substrate in the invention is preferably a high wet strength wet laid nonwoven substrate comprising a mixture of cotton and rayon fibres with a basic weight in the range from 35 gsm. to 85 gsm. providing a good pleasant and substantive feel to the skin and retaining sufficient strength when wetted in use, but yet being not too substantive as to make the user reluctant to dispose of the article after single use. Other substrate can be envisaged comprising of different fibre composition and different basis weights which would be equally suitable for use in the current invention.

The substrate is impregnated with a surfactant composition comprising a mixture of anionic surfactants, foam boosters, super fatting agents, fungicides and other ingredients suspended in water at a total solids content in the range from 20% to 70% and perferably in the range from 40% to 70%, and with a viscosity in the range from 50 cps. to 1,000 cps. and preferably in the range from 100 cps to 300 cps. The components of the composition must all be suitable for use in personal washing.

There are many possible anionic surfactants but we prefer to use a fatty alcohol polyglycol ether sulphosuccinate, which, unlike other well known anionic surfactants, can be manufactured at concentrations of up to 40% solids in water and still retain very low viscosities which are ideal for easy impregnation, in contrast to other types where 25% to 30% solids contents only are achievable without the composition becoming so viscose as to prevent simple impregnation being achieved easily. The foam boosters, super fatting agents and other ingredients are chosen from amongst those commonly used in hair and body shampoos, but chosen from those groups which do not show marked viscosity modifying behaviour. A colourant may advantageously be added to the composition, to impart a pleasant appearance to the product and provide an indication of useage.

The preferred manufacturing method is to pass the non woven substrate through a dip tank containing the surfactant composition and then between a pair of nipping rollers to provide even impregnation and metered impregnation dosage. The final ratio after drying and detergent composition to substrate is perferably between 1:1 and 10:1 by weight. The wet impregnated substrate is then passed through a drying stage before rewinding and other operations needed to convert the parent web into end product. It can thus be seen that surfactant compositions well suited to the present invention are those showing high solids in water content at low viscosity. After drying, 0.5% to 5% by weight of a perfume composition is added onto the product.

Other manufacturing methods can be envisaged which are well known including spray coating, and methods which rely on solvent based surfactant compositions. It is also possible to formulate satisfactory compositions that are solid in nature at normal ambient temperatures and that are applied to the nonwoven substrate in a moltent state and cooled to give the end product.

An embodiment of the invention will now be described by way of example only, without limiting the invention.

The product is a personal cleansing cloth for use during showering comprising of a sheet of nonwoven substrate 300 mm long and 250 mm wide.

The nonwoven substrate of the example is a wet laid nonwoven consisting of a mixture of cellulose and rayon fibres with an acrylic binder, with characteristics of weight 60 grammes per square metre, thickness 275 micro and density 200 kg per cubic metre, such as Storalene 741/60 produced by Stora Kopparburg Bergvik Ltd.

The sheet was impregnated with a surfactant composition comprising of a blend of di sodium lauryl alcohol polyglycol ether sulphosuccinate as principle detergent, coconut diethanolamide acting as a foam booster, ricinoleic acid alkanolamide sulphosuccinate acting as a super fatting agent and undecylenic acid propylamido trimethyl ammonium methosulphate acting as a fungicide. These are all available from REWO Chemicals Ltd. This composition is 48% solids when formulated, and 9.4 g of this was impregnated onto the sheet of nonwoven substrate by passing the substrate through a dip tank containing the surfactant composition and out through a nipping roller arrangement to meter the impregnation level exactly, and then dried in a hot air assisted oven leaving 4.5 g of solids on the cloth.

The resultant dry cloth was impregnated with 0.5% by weight of a perfume composition in an alcohol base to impart a pleasant odour to the product.

The article in this example is particularly advantageous for use in the shower as it produces a rich stable foam in both hot and cold water, and imparts a refreshing clean feeling to the hair and skin after use. The nonwoven substrate is sufficiently bulky and strong as to prevent break up during use and because of its nature can be used to produce the product relatively cheaply so that it may be used once and then discarded.

It is to be understood that various impregnated cloths have been described in the past such as for example those impregnated with fabric softening compounds. However, the materials used in these cloths render them quite unsuitable for use as personal washing articles in accordance with the concept of the present invention.

I claim:

1. A disposable personal washing cloth comprising a substrate of high wet-strength nonwoven material impregnated with a surfactant composition containing a fatty alcohol polyglycol ether sulphosuccienate, said impregnated substrate being dried for presentation dry to a user for use as a hair and/or body shampoo and wash cloth when wet.

2. A washing cloth according to claim 1, wherein the non-woven material comprises a mixture of cotton and rayon fibres.

3. A washing cloth according to claim 1, wherein the non-woven material has a basic weight in the range from 35 gsm to 85 gsm.

4. A washing cloth according to claim 1, wherein the surfactant composition also includes a foam booster, a super fatting agent and a fungicide, suspended in water.

5. A washing cloth according to claim 4, wherein the composition has a total solids content in the range from 20% to 70%.

6. A washing cloth according to claim 5, wherein the total solids content is in the range from 40% to 70%.

7. A washing cloth according to claim 1, wherein the viscosity of the composition used for impregnating the material is in the range from 50 cps to 1,000 cps.

8. A washing cloth according to claim 7, wherein the viscosity is in the range from 100 cps to 300 cps.

9. A method of manufacturing a disposable personal washing cloth, comprising the steps of impregnating a non-woven substrate by passing it through a dip tank containing a surfactant composition comprising a fatty alcohol polyglycol ether sulphosuccinate, metering the impregnation level of said substrate by passing it between a pair of nipping rollers, and thereafter drying said impregnated substrate.

10. A method according to claim 9, wherein the ratio, after drying, of said surfactant composition to substrate is between 1:1 to 10:1 by weight.

* * * * *